United States Patent
Nakata et al.

(10) Patent No.: US 7,724,382 B2
(45) Date of Patent: May 25, 2010

(54) METHOD AND APPARATUS FOR IRRADIATING LASER

(75) Inventors: Mitsuru Nakata, Tokyo (JP); Hirofumi Shimamoto, Tokyo (JP); Hiroshi Kanoh, Tokyo (JP)

(73) Assignees: NEC Corporation, Tokyo (JP); NEC LCD Technologies, Ltd., Kanagawa (JP)

( * ) Notice: Subject to any disclaimer, the term of this patent is extended or adjusted under 35 U.S.C. 154(b) by 497 days.

(21) Appl. No.: 11/737,640

(22) Filed: Apr. 19, 2007

(65) Prior Publication Data

US 2007/0249134 A1 Oct. 25, 2007

(30) Foreign Application Priority Data

Apr. 19, 2006 (JP) ............... 2006-115710

(51) Int. Cl.
*G01B 11/00* (2006.01)
*G01B 11/28* (2006.01)
*G01J 3/46* (2006.01)

(52) U.S. Cl. ............. 356/629; 356/425; 356/408; 356/388; 356/398; 438/14

(58) Field of Classification Search ......... 356/601–608, 356/625, 630, 636–640, 402–408, 445–448, 356/629, 425; 438/14–18
See application file for complete search history.

(56) References Cited

U.S. PATENT DOCUMENTS

| | | | | |
|---|---|---|---|---|
| 5,982,482 A * | 11/1999 | Nelson et al. | ............ | 356/237.1 |
| 6,218,198 B1 * | 4/2001 | Imao et al. | ............ | 438/7 |
| 6,396,299 B1 * | 5/2002 | Hayashida | ............ | 324/770 |
| 6,975,386 B2 * | 12/2005 | Tsumura et al. | ............ | 356/30 |
| 7,102,750 B2 * | 9/2006 | Takami | ............ | 356/432 |
| 7,289,233 B2 * | 10/2007 | Kurokawa et al. | ............ | 356/630 |
| 7,312,418 B2 * | 12/2007 | Tanabe et al. | ............ | 219/121.65 |

FOREIGN PATENT DOCUMENTS

| JP | 10-173014 | 6/1998 |
|---|---|---|
| JP | 2000-114174 | 4/2000 |
| JP | 2002-008976 | 1/2002 |
| JP | 2002-98634 | 4/2002 |
| JP | 2002-340812 | 11/2002 |
| JP | 2003-332346 | 11/2003 |
| JP | 2006-32835 | 2/2006 |

* cited by examiner

*Primary Examiner*—Sang Nguyen
(74) *Attorney, Agent, or Firm*—Dickstein Shapiro LLP (57) ABSTRACT

A laser irradiation process includes: scanning a substrate with laser having a predetermined lasing frequency at different irradiation intensities to form a plurality of first irradiation areas corresponding to the irradiation intensities; illuminating the first irradiation areas to reflected light receive from the fist irradiation areas; determining microcrystallization intensity based on the received reflected light; and determining irradiation intensity based on the thus determined microcrystallization intensity. The laser irradiation process uses the irradiation intensity for irradiating a polycrystalline film in a product semiconductor device.

14 Claims, 6 Drawing Sheets

METHOD AND APPARATUS FOR IRRADIATING LASER

This application is based upon and claims the benefit of priority from Japanese patent application No. 2006-115710, filed on Apr. 19, 2006, the disclosure of which is incorporated herein in its entirety by reference.

BACKGROUND OF THE INVENTION

1. Field of the Invention

The present invention relates to a method and apparatus for irradiating laser and, more particularly, to the technique such as used in a laser annealing process performed for forming g a polycrystalline thin film by irradiating a semiconductor thin film with a laser.

2. Description of the Related Art

A polycrystalline silicon thin film (referred to as polycrystalline-Si film hereinafter) is adopted as a conductive film of a thin-film-transistor (TFT) device formed on a glass substrate because of the easiness for processing. Generally, an excimer laser annealing (ELA) technique is employed to form the polycrystalline-Si film. In the ELA process, an amorphous silicon in film (referred to as amorphous-Si film hereinafter) is formed on the substrate, and a pulse beam of excimer laser is irradiated on the thus formed amorphous-Si film. The amorphous-Si film is melted by the irradiation of the laser, and then recrystallized through a cooling down, consequently to form a polycrystalline-Si film. It is generally known that a larger grain size of the polycrystalline-Si film provides excellent properties for the TFT device, especially in the carrier mobility thereof. Therefore, it is desired to form the crystal grain as large as possible in the polycrystallization of the amorphous-Si film.

In the process of polycrystallizing the amorphous-Si film, along with an increase in the irradiation intensity of laser, a shift is caused from a crystallization (ordinary crystallization) wherein a relatively large crystal grain is obtained toward a microcrystallization wherein a finer crystal grain is obtained. The ordinary crystallization is caused when the amorphous-Si film is not completely melted, and thus nuclei are generated at random at the boundary surface between the solid phase and the liquid phase of silicon or the boundary surface between the amorphous-Si film and the substrate, during the recrystallization. In the ordinary crystallization, the diameter of the crystal grain increases as the irradiation intensity is increased.

On the other hand, the microcrystallization is caused when the is amorphous-Si film is completely melted, and thus nuclei are generated in a relatively uniform state in the entire film, during the recrystallization. The diameter of the crystal grain created in the microcrystallization is as small as 100 nm or below. In the microcrystallization, the diameter of the crystal grain scarcely depends on the irradiation intensity. The threshold intensity of the laser at which the shift from the ordinary crystallization toward the microcrystallization occurs is referred to as "microcrystallization intensity". The microcrystallization intensity is a parameter normalized by the thickness of the amorphous-Si film in general.

As described above, in the process of polycrystallizing the amorphous-Si film, the shift from the ordinary crystallization toward the microcrystallization, bounded by the microcrystallization intensity, is abruptly caused with an increase in the irradiation intensity of the laser. That is, when the irradiation intensity of the laser exceeds the microcrystallization intensity, the grain size of the resultant polycrystalline-Si film extremely reduces, whereby a suitable grain size is not achieved. Therefore, in the process of polycrystallizing the amorphous-Si film, it is important to accurately determine the microcrystallization intensity and set the irradiation intensity of the laser smaller than the microcrystallization intensity.

Patent Publications JP-2000-114174A and JP-2002-8976A describe a technique for determining the microcrystallization intensity. According to these patent publications, prior to actual irradiation for forming a polycrystalline-Si film in a TFT device, preliminary irradiation is performed in which the laser is irradiated on a pulse-by-pulse basis onto preliminary irradiation areas provided outside a target irradiation area, on which the TFT device is to be formed. The preliminary irradiation is performed while moving the irradiation position and changing the irradiation intensity within a range over and below the melting intensity of the amorphous-Si film. The relationship between the irradiation intensity and the presence/absence of microcrystallization is derived from the spectral measurement of a Raman light or scattered light for the preliminary irradiation areas, and the radiation intensity at which the microcrystallization starts is determined to be the microcrystallization intensity.

According to the technique of the above patent publications, the actual radiation is performed by irradiating the laser at the intensity lower than the microcrystallization intensity thus determined, which allows the microcrystallization of the amorphous-Si film to be prevented. In the technique of these documents, however, the spectral measurement of a Raman light or scattered light must be performed while the light source for measurement and the light-receiving position for the reflected light are moved to respective preliminary irradiation areas. This impedes improvement in throughput of forming the polycrystalline-Si film.

SUMMARY OF THE INVENTION

It is therefore an exemplary object of the present invention to provide laser irradiation method and apparatus for crystallizing a semiconductor film, which is capable of providing a resultant film having a relatively large g size and improving the throughput therein.

It is another exemplary object of the present invention to provide a method and apparatus for detecting a microcrystallization intensity of laser irradiated for crystallizing a semiconductor film.

It is a further exemplary object of the present invention to provide a method for judging a grain size of a polycrystalline film.

The present invention provides, in a first aspect thereof, a method including: scanning a semiconductor film on a substrate with laser having a specific lasing frequency at a plurality of irradiation intensities to form a plurality of irradiation areas on the semiconductor film each corresponding to one of the irradiation intensities; illuminating the plurality of irradiation areas in block to receive light reflected from the irradiation areas in block; judging a microcrystallization intensity based on the received reflected light; determining an irradiation intensity based on the microcrystallization intensity; and scanning another semiconductor film with laser having the lasing frequency at the determined irradiation intensity to form a crystallized film.

The present invention provides, in a second aspect thereof, a method including: scanning a semiconductor Mm on a substrate with laser having a specific lasing frequency at a plurality of irradiation intensities to form a plurality of irradiation areas on the semiconductor film each corresponding to one of the irradiation intensities; illuminating the plurality of irradiation areas in block to receive light reflected from the irradiation areas in block; and measuring chromaticity of the received reflected light for each of the irradiation areas to detect a microcrystallization intensity based on the measured chromaticity.

The present invention provides, in a third aspect thereof, a method including: illuminating an area of a polycrystalline film to receive light reflected from the area; dividing the area into a plurality of divided areas and measuring chromaticities of the received reflected light for the divided areas; and comparing the measured chromaticities against one another to judge a uniformity of chromaticity among the measured chromaticities; and judging a uniformity of a grain size of the polycrystalline film based on the judged uniformity.

The above and other objects, features and advantages of the present invention will be more apparent from the following description, referring to the accompanying drawings.

DETAILED DESCRIPTION OF THE PREFERRED EMBODIMENTS

Now, exemplary embodiments of the resent invention will be described with reference to accompanying drawings, wherein similar constituent elements are designated by similar reference numerals throughout the drawings.

Figure 1:
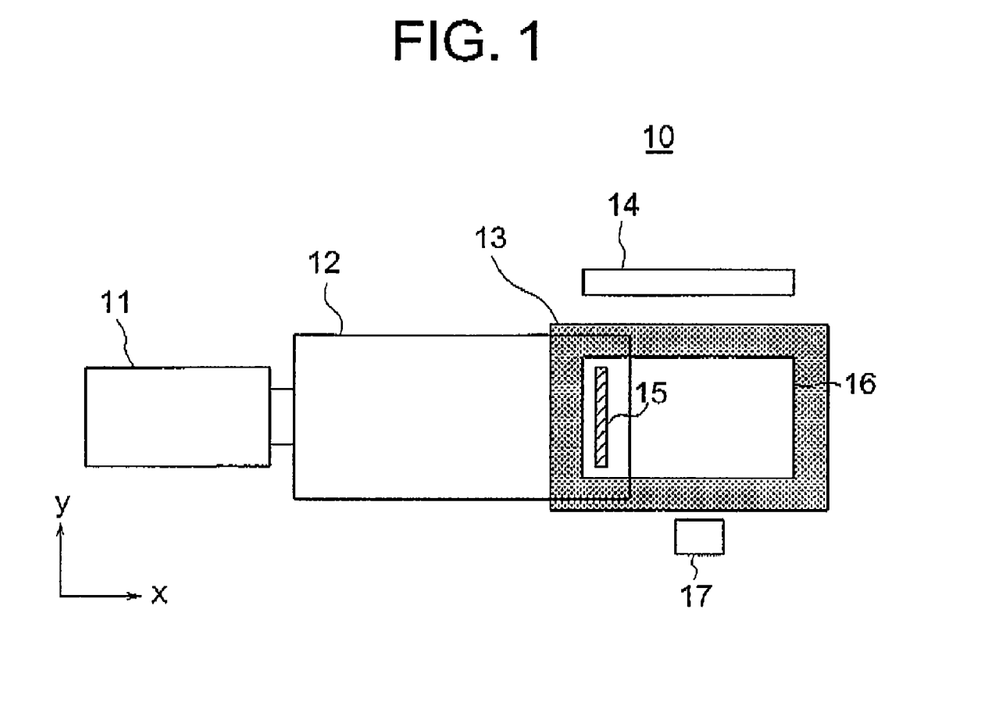
FIG. 1 is a top plan view showing the configuration of a laser irradiation apparatus used for a laser irradiation method according to a first embodiment of the present invention.

FIG. 1 is a top plan view showing the configuration of a laser irradiation apparatus, generally designated by numeral 10, for use in a laser irradiation method according to a first embodiment of the present invention. The laser irradiation apparatus 10 includes a laser source 11, an optical system 12, a stage 13, a surface-light source unit 14 and an optical sensor configured by a charge coupled device 17. The laser irradiation apparatus 10 is used for melting and recrystallizing an amorphous-Si film formed on a surface of a substrate 16 to form a polycrystalline-Si film therefrom.

The laser source 11, which is an excimer laser device, generates a pulse laser having a predetermined lasing frequency toward the direction denoted by "x". The optical system 12 forms the laser 15 irradiated from the, laser source 11 into an elongated rectangular shape, or linear shape, extending along the direction denoted by "y". The substrate 16 is placed on the stage 13, and the rectangular-shaped laser is irradiated onto the surface of the substrate 16. The stage 13 is allowed to move in both the x- and y-directions in the state that the substrate 16 is placed thereon.

Figure 2:
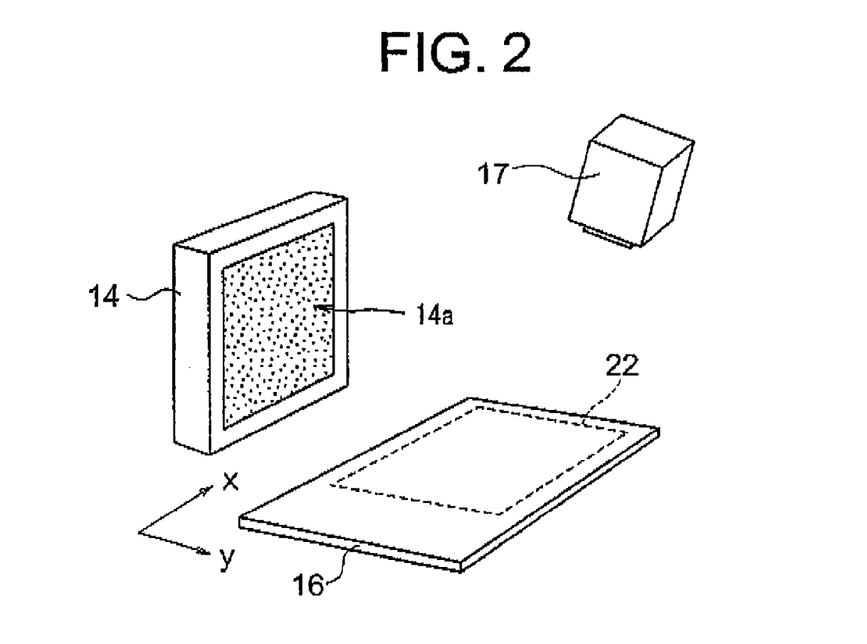
FIG. 2 is a perspective view showing the positional relationship among the surface-light source it, the substrate and the charge coupled device shown in FIG. 1.

FIG. 2 is a perspective view showing the positional relationship among the surface-light source unit 14, the substrate 16 placed on the stage 13 and the charge coupled device 17 shown in FIG. 1. The surface-light source unit 14 has a rectangular emitting surface 14a. The surface-light source unit 14 is arranged so that the light emitting surface 14a makes an acute angle with respect to the surface of the substrate 16. A white flat light emitted in the direction perpendicular to the light emitting surface 14a and having an approximately uniform intensity in the in-plane direction is irradiated from the light emitting surface 14a. The flat light emitted from the light emitting surface 14a illuminates a predetermined area, or illumination area 22, of the surface of the substrate 16. In this illumination, the, flat light irradiates respective portions of the illumination area 22 at a uniform intensity and a uniform incidence angle. The charge coupled device 17 includes charge coupled elements capable of imaging three different colors including red, green and blue, and receives the reflected light from the entire illumination area 22 in block for an image pick-up operation.

Figure 3:
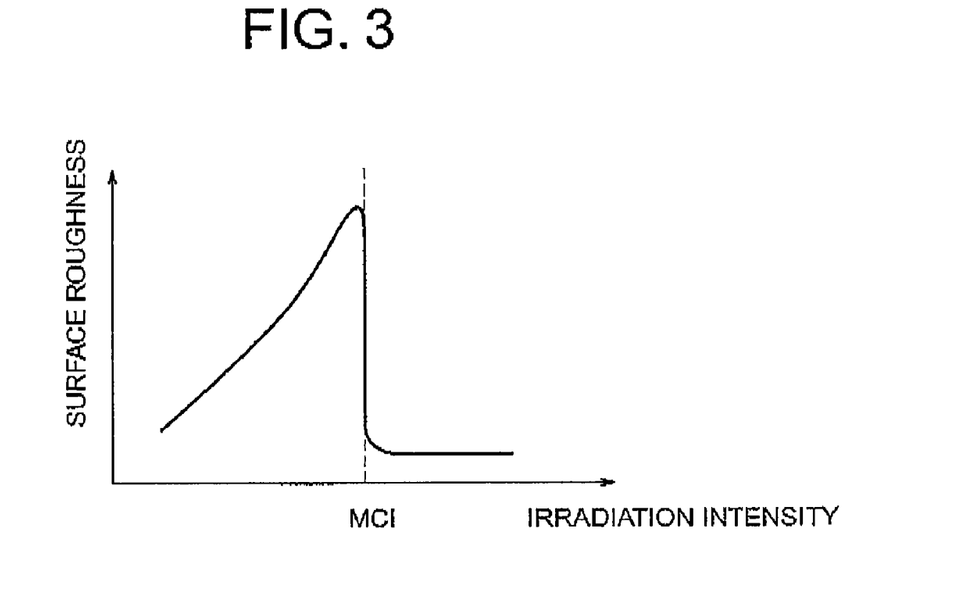
FIG. 3 is a graph showing the relationship between the irradiation intensity and the surface roughness of the polycrystalline-Si film.

FIG. 3 is a graph showing the relationship between the irradiation intensity of the laser and the degree of concavity and convexity, or the surface roughness of the top surface of the polycrystalline-Si film, which represents the size of the crystal grain in tie resultant film. As shown in FIG. 3, along with the increase in the irradiation intensity, the surface roughness increases until the irradiation intensity reaches the microcrystallization intensity. However, if the irradiation intensity exceeds the microcrystallization intensity, the surface roughness abruptly decreases. Meanwhile, the degree of the surface roughness significantly affects the chromaticity of the light reflected from the surface of the polycrystalline-Si film. Especially, the chromaticity of tie top surface of the polycrystalline-Si film changes drastically with the microcrystallization intensity being the boundary. Based on this fact the microcrystallization intensity is determined by using the chromaticity detected by the charge coupled device 17 in the present embodiment.

Figure 4:
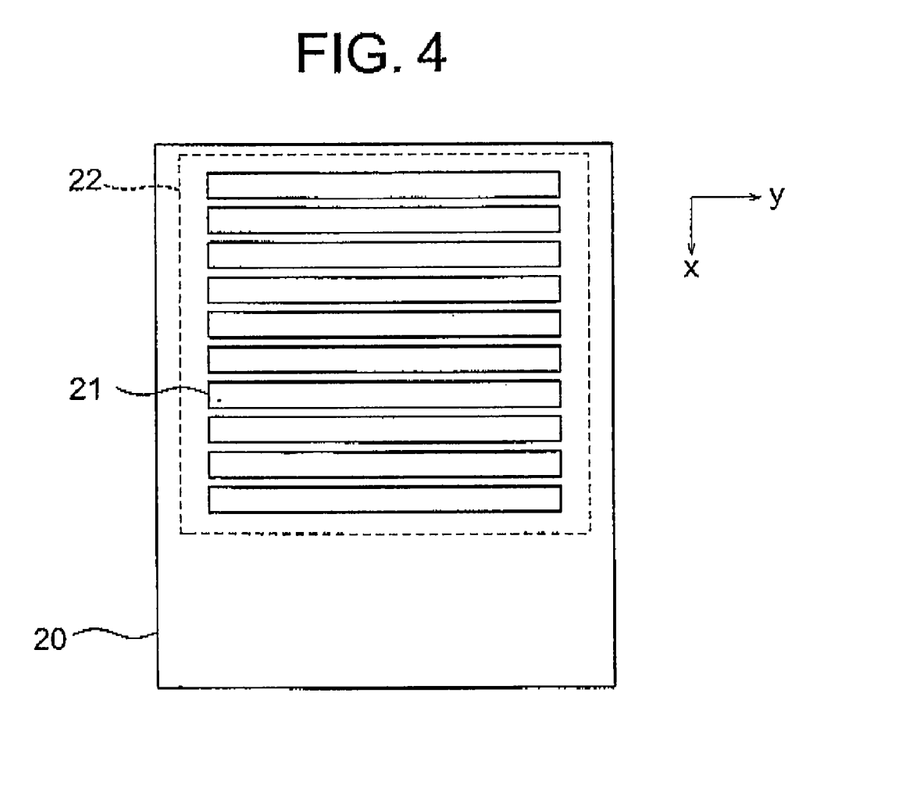
FIG. 4 is a top plan view showing the configuration of a substrate for use in determining the microcrystallization intensity.

In the laser irradiation process of the present embodiment, a preliminary irradiation is performed on a microcrystallization-intensity judgment substrate 20 for the purpose of determining the microcrystallization-intensity, prior to the irradiation of a laser (actual irradiation) onto a target substrate on which the polycrystalline-Si film is formed. FIG. 4 is a top plan view showing the configuration of the microcrystallization-intensity judgment substrate 20. On the surface of the microcrystallization-intensity judgment substrate 20, an amorphous-Si film is formed in advance using the process conditions similar to the process conditions in which tie polycrystalline-Si film is formed on the target substrate for the product. On the amorphous-Si film formed on the microcrystallization-intensity judgment substrate 20, a plurality of preliminary irradiation areas 21 having an elongated rectangular shape extending in the y-direction are arranged in the x-direction to form an array. The illumination area 22 includes a plurality of these preliminary irradiation areas 21.

Figure 5:
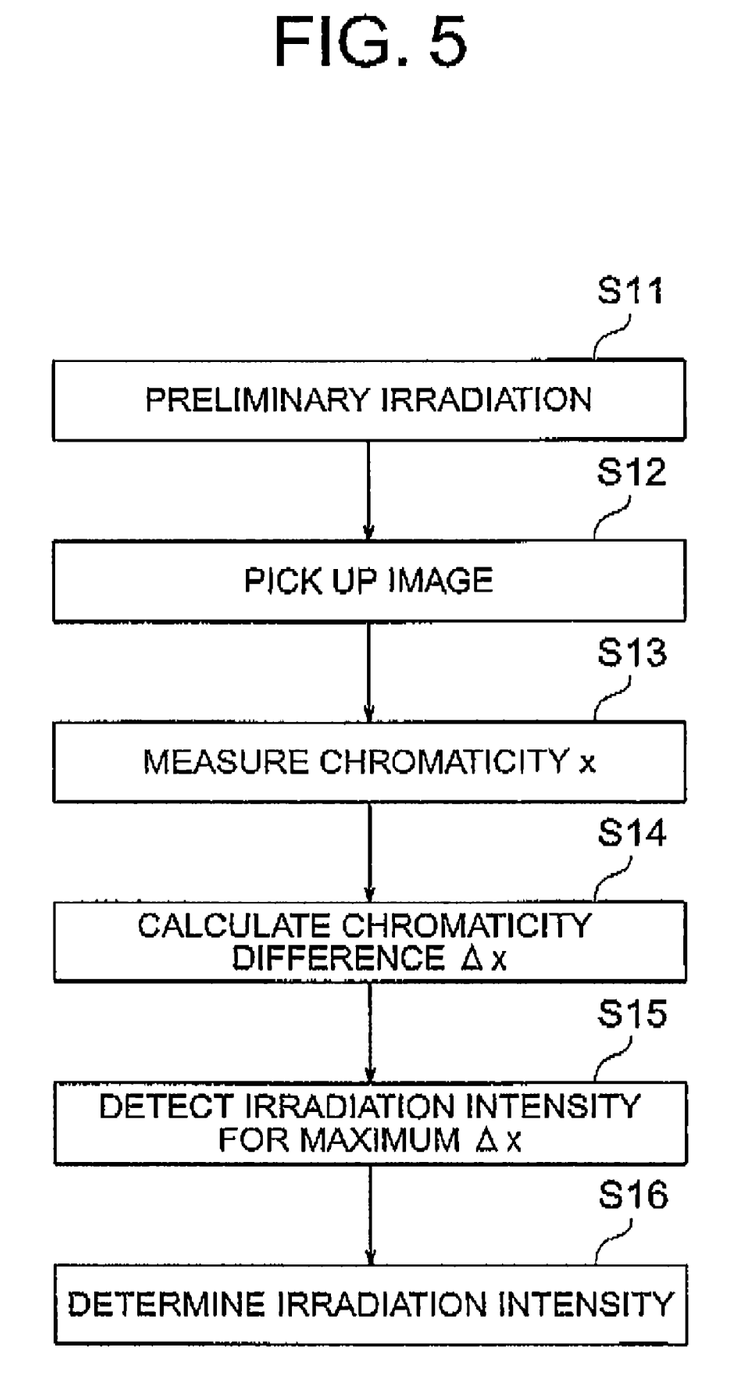
FIG. 5 is a flowchart showing the procedure of a laser irradiation process according to the first embodiment.

FIG. 5 is a flowchart showing the procedure of the laser irradiation process of the present embodiment. The substrate 20 is placed on the stage 13, and thereafter, the plurality of preliminary irradiation areas 21 are irradiated with laser of different irradiation intensities within the range above and below the melting intensity of the amorphous-Si film (step S11). Subsequently, the surface-light source unit 14 irradiates the illumination area 22 of the substrate 20, and at the same time, the, charge coupled device 17 picks-up the image of the illumination area 22 in block (step S12). Further, the chromaticity of each of the preliminary irradiation areas 21 is measured from the image data acquired by the image-pickup operation, and the measured chromaticity is evaluated for the value thereof (step S13). In the evaluation of the chromaticity, x-component chromaticity (chromaticity x) of the CIE (Commission Internationale d'Eclairage)-XYZ color system is used.

Subsequently, the relationship between the irradiation intensity and the amount of change, or chromaticity difference Δx effected in the chromaticity x is calculated with respect to change in the irradiation intensity, based on the relationship between the evaluated chromaticity x and the irradiation intensity (step S14). Further, the irradiation intensity where the change in the chromaticity x, i.e., the chromaticity difference Δx assumes a maximum is detected and determined as the microcrystallization intensity (step S15). In this step, a maximum change in the chromaticity per unit change of said irradiation intensity can be detected. Automated operation is performed using a computer to evaluate the chromaticity x, calculate the relationship between the chromaticity difference Δx and the irradiation intensity, and detect the irradiation intensity at which the chromaticity difference Δx assumes a maximum. The irradiation intensity to be used in the actual irradiation is determined based on the determined microcrystallization intensity (step S16).

Figure 6A:
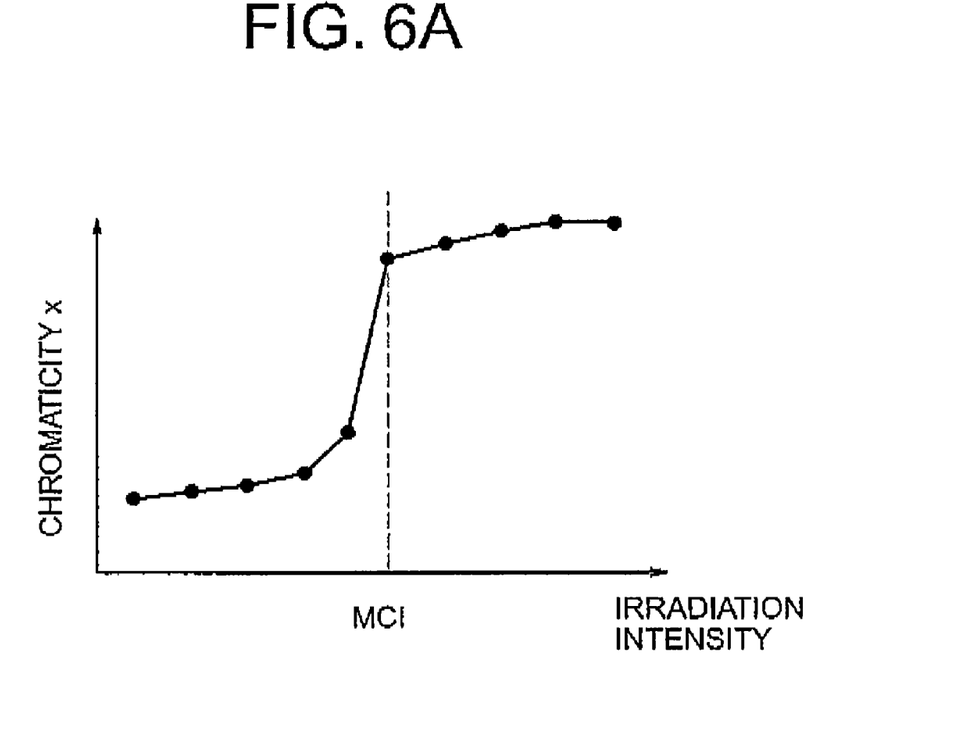
FIG. 6A is graph showing the relationship between the chromaticity x and the irradiation intensity.
Figure 6B:
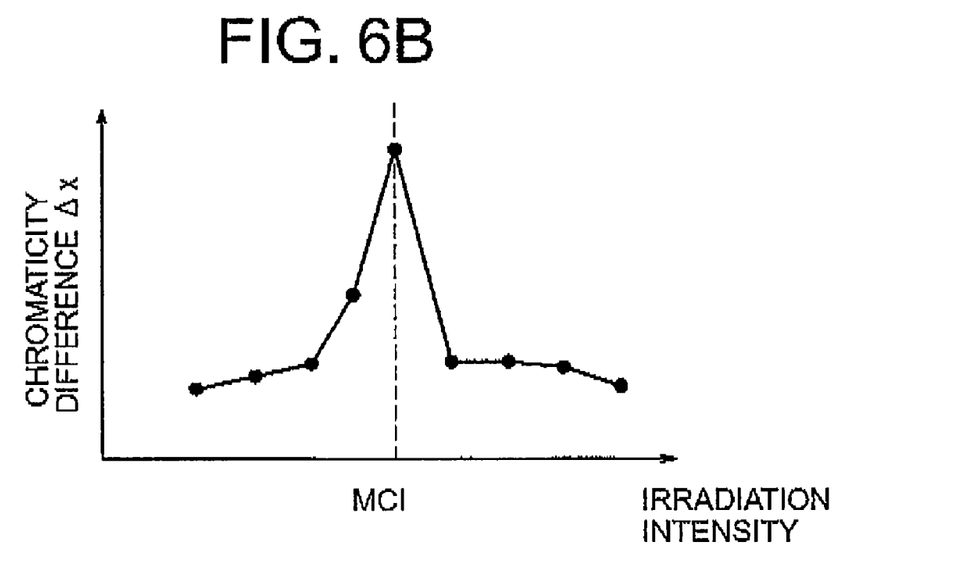
FIG. 6B is a graph showing the relationship between the chromatic difference Δx and the irradiation intensity.

FIG. 6A is a graph showing the relationship between the irradiation intensity and the chromaticity x measured for each of the preliminary irradiation areas 21. FIG. 6B is a graph showing the relationship obtained from FIG. 6A between the chromaticity difference Δx and the irradiation intensity. As understood from FIG. 6A, the chromaticity x increases along with the increase in the irradiation intensity, showing an abrupt increase in the vicinity of the microcrystallization intensity (MCI). As understood from FIG., 5B, the chromaticity difference Δx has a maximum at the microcrystallization intensity. Thus, it is possible to accurately determine the microcrystallization intensity by judging that the irradiation intensity at which fie chromaticity difference Δx is maximized is the microcrystallization intensity.

In the laser irradiation process of the present embodiment, the illumination area 22 is picked-up for image in block when the illumination area 22 is illuminated, whereby the light reflected from the preliminary irradiation areas 21 can be simultaneously received. This eliminates the necessity of moving the stage 13 or the charge coupled device 17 for the determination of microcrystallization intensity, thereby improving the throughput of the process. In addition, since the equipment necessary for moving the stage 13 or the charge coupled device 17 is not required, a cost reduction is also achieved. The image-pickup of the illumination area 22 is performed by receiving the light reflected from the entire preliminary irradiation areas 21 in block. Thus, the number of pixels of the charge coupled device 17 can be reduced.

By determining that the irradiation intensity at which the chromaticity difference Δx assumes a maximum is the microcrystallization intensity, the microcrystallization intensity can easily and accurately be determined. Since this allows adoption of an irradiation intensity which is below the microcrystallization intensity in the actual recrystallization for the product, it is possible to form a polycrystalline-Si film having a relatively large grain size without incurring the undesirable microcrystallization. Thus, a TFT device having excellent characteristics such as a higher carrier mobility can be obtained.

It is desirable for the irradiation intensity on the substrate to be uniform in the in-plane direction, in order for suppressing errors from occurring during measuring the chromaticity. For this purpose, it is preferable that the area of the light emitting surface 14a of the surface-light source unit be larger than the total area of the plurality of preliminary irradiation areas 21. In addition, it is preferable that the range of variation in the in-plane luminance of the light emitting surface 14a be 5% or less.

In the embodiment described above, the microcrystallization-intensity judgment substrate 20 is provided separately from the target substrate for use in a product. It is also possible to use the same substrate and provide therein the preliminary irradiation areas 21 and the area for actual irradiation separately. Further, the x-component of the CIE-XYZ color system is used for evaluating the chromaticity. However, it is also possible to use y-component, or both the x-component and y-component. Furthermore, in the determination of microcrystallization intensity, it is also possible to evaluate the luminance in stead of the chromaticity.

Figure 7:
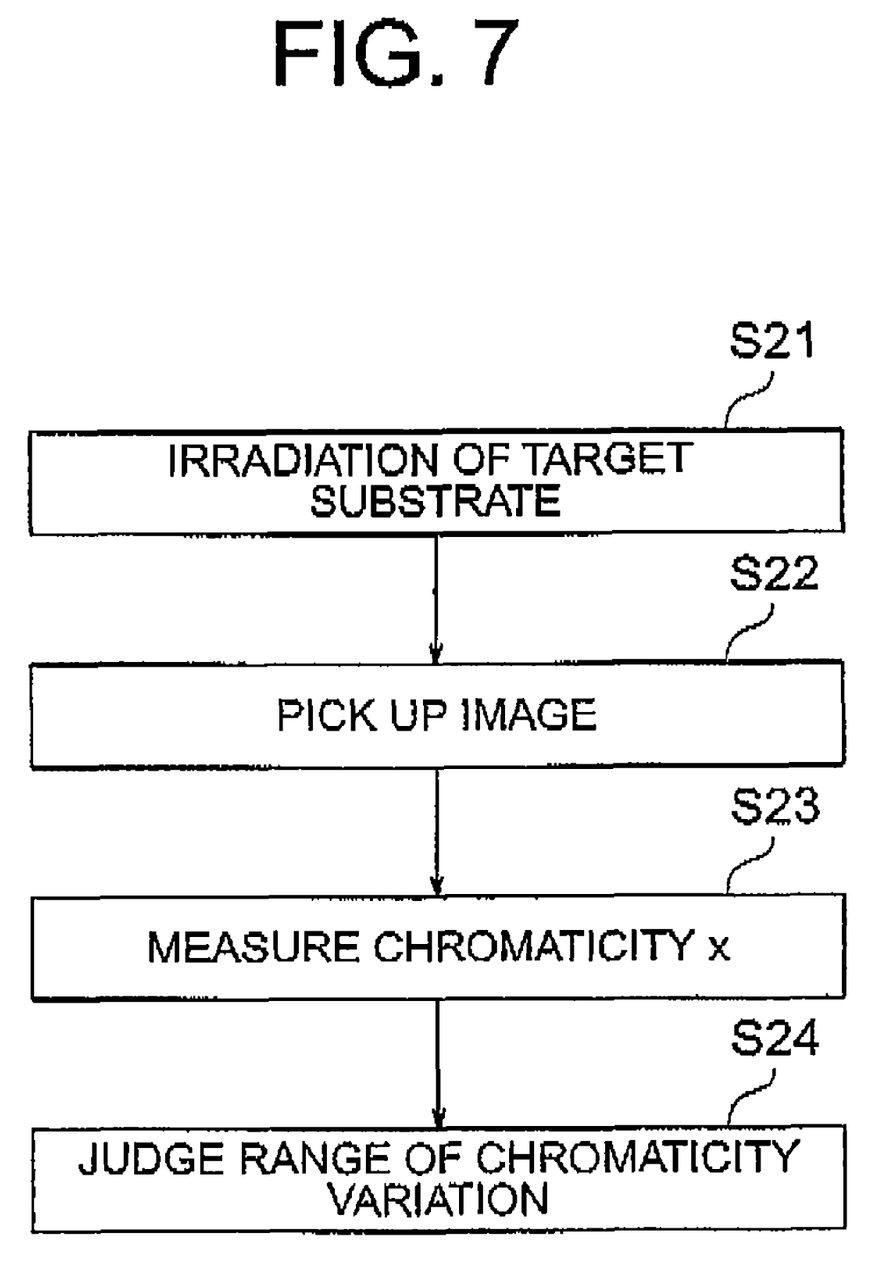
FIG. 7 is a flowchart showing the procedure of a method of judging the grain size uniformity according to a second embodiment of the present invention.

FIG. 7 is a flowchart showing the procedure of a method for judging the size uniformity in a laser irradiation process according to a second embodiment of the present invention, In the method of the present embodiment, judged is the uniformity of the grain size of the polycrystalline-Si film formed by a laser irradiation. First, the laser irradiation apparatus shown in FIG. 1 is used, where the substrate for a product is placed on the stage 13, and the actual irradiation is performed to form a polycrystalline-Si film of the TFT devices (step S21). To form the polycrystalline-Si film, the irradiation intensity of laser is set lower than the microcrystallization intensity.

Next, while allowing the surface-light source unit 14 to illuminate the target irradiation area which has been irradiated by laser, the charge coupled device 17 picks-up the image of the target irradiation area in block (step S22). A plurality of judgment regions are set within the target irradiation area, and the chromaticity of each of the judgment regions is measured from the image data acquired by the image-pickup operation for evaluation (step S23). In the process of evaluating the chromaticity, similarly to, e.g., the first embodiment, the x component (chromaticity x) in the CIE-XYZ color system is used. Subsequently, the range of variation in the chromaticity x (chromaticity variation) is calculated from the measured chromaticity x in the respective judgment regions, and this range of chromaticity variation is determined as the range of variation in the grain size (grain size uniformity) (step S24). In order to suppress possible errors in the measurement of the chromaticity, the light emitting surface 14a of the surface-light source unit is set larger in area than the target irradiation area.

In the method of judging the grain size uniformity in the present embodiment, the image of the target irradiation area is picked-up in block while the area is illuminated, whereby the light reflected from the respective judgment regions is simultaneously received. This eliminates, similarly to the first embodiment, the necessity of moving the stage 13 or the charge coupled device 17 in the determination of grain size uniformity, thereby improving the throughput of the process. In addition, the equipment necessary for moving the stage 13 or the charge coupled device 17 is not required, thereby achieving a cost reduction. The image pickup of the target irradiation area can be performed by receiving the light reflected from the entire judgment regions in block. Thus, the number of pixels of the charge coupled device 17 can be reduced.

Since the grain size uniformity is acquired from the range of variation in the chromaticity, the in-plane grain size uniformity in the target irradiation area can easily and accurately be judged. Based on the grain size uniformity thus judged, the range of in-plane variation in the irradiation intensity and film-forming conditions of the laser are corrected, thereby providing a polycrystalline-Si film having a smaller range of in-plane variation in the grain size. Accordingly, TFT devices having a smaller range of characteristic variation can be formed and product yield thereof is improved. Assuming that the process conditions for forming the film are uniform in the in-plane direction of the film in the target irradiation area, the in-plane variation of the grain size obtained in the target irradiation area in the second embodiment provides judgment of the range of in-plane variation for tie laser irradiation intensity.

It is to be noted that although the preliminary irradiation and actual irradiation are performed on the same stage 13 in the embodiments described above, these irradiations can be performed on different stages. Further, in the laser irradiation apparatus 10, for example, the actual irradiation can be repeatedly performed under the same irradiation condition, whereby the relationship between the number of irradiation times of laser and the chromaticity of the light reflected from the target irradiation area are examined. This can determine the degree of reduction in the irradiation intensity of the laser. The decrease and range of in-plane variation in the irradiation intensity of laser occur by, e.g., a stain of the optical system 12.

Figure 8:
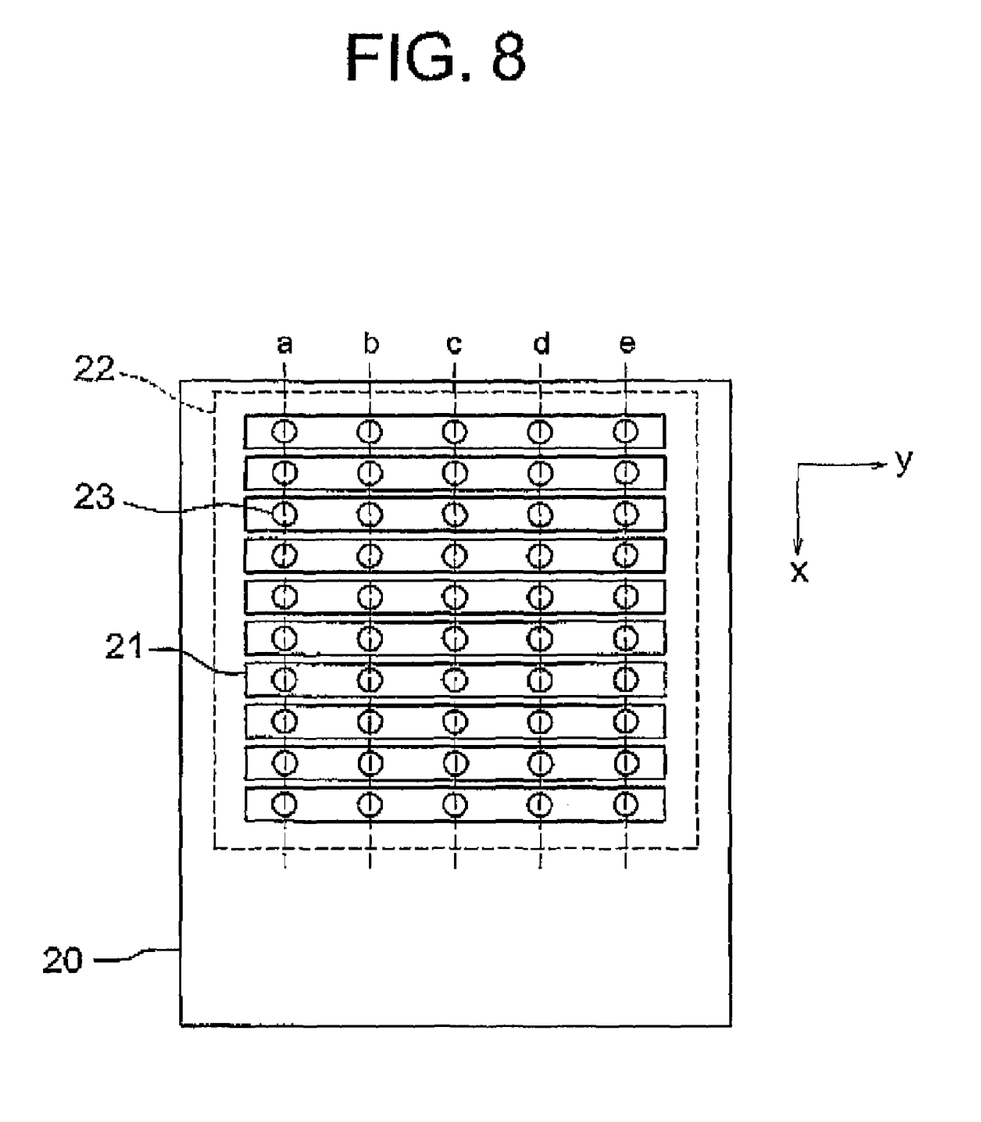
FIG. 8 is a top plan view showing the substrate used in determining the microcrystallization intensity used in the first embodiment.

A first example based on the laser irradiation process of the first embodiment will now be described. FIG. 8 is a top plan view showing the configuration of the microcrystallization-intensity judgment substrate used in the fist example. A glass substrate having a 370 mm×470 mm size was prepared. A $SiO_2$ film was formed having a thickness of 2000 angstroms on the glass substrate, and an amorphous-Si film was formed having a thickness of 500 angstroms on the $SiO_2$ film thereby achieving the microcrystallization-intensity judgment substrate 20.

A plurality of preliminary irradiation areas 21 of the microcrystallization-intensity judgment substrate 20 thus formed were irradiated with pulse laser having different irradiation intensities within the range above and below the melting intensity of the amorphous-Si film. The pulse laser was used to scan the plurality of preliminary irradiation areas 21 in the x-direction, whereby the entire preliminary irradiation areas 21 were irradiated with the pulse laser. The lasing frequency of the pulse laser was 300 Hz, and the dimensions of the irradiated laser were 350 mm (in y-direction)×0.4 mm (in x-direction). The scanning pitch was 0.04 mm so that the irradiated laser beams overlap one another at the overlapping rate of 90%.

Each preliminary irradiation area 21 has a 350 mm (in y-direction)×20 mm (in x-direction) size, with the space between adjacent preliminary irradiation areas 21 was set at 1 mm. The irradiation intensity was varied within the range of 445 to 490 $mJ/cm^2$, with the irradiation intensity being changed at a uniform step of 5 $mJ/cm^2$ between adjacent preliminary irradiation areas 21. Further, the illumination area 22 was picked-up for image thereof by the charge coupled device 17 while being irradiated with a while light. The charge coupled device 17 having 400,000 pixels was used for the image pick-up operation.

In this example, five judgment regions 23a to 23e were provided in each of the preliminary irradiation areas 21. The judgment regions 23a to 23e of each of tie preliminary irradiation areas 21 were arranged at a regular interval in the y-direction and aligned in the x-direction with the judgment regions 23a to 23e, respectively, in the other preliminary irradiation areas 21. In other words, the corresponding judgment regions 23a, for example, aligned in the x-direction configure a group of judgment regions. The diameter of the judgment regions 23a to 23e was set at 10 mm The chromaticity x was numerically expressed for each of the judgment regions 23a to 23e of the preliminary irradiation areas 21 based on the image data obtained therefrom. The relationship between the chromaticity difference Δx and the irradiation intensity in each group was calculated based on the numerically-expressed chromaticity x.

As a result of the above process, both the relationship between the chromaticity x and the irradiation intensity and the relationship between the chromaticity difference Δx and the irradiation intensity for each group of the judgment regions 23a to 23e revealed a similar tendency, such as shown in FIGS. 6A and 6B. However, due to the range of in-plane variation in, the irradiation intensity of the pulse laser beams, for the case of groups of the judgment regions 23a to 23c, the chromaticity x increased abruptly and the chromaticity difference Δx assumed a maximum both at an irradiation intensity of 470 $mJ/cm^2$. On the other hand, for the case of groups of the judgment regions 23d and 23e, the chromaticity x increased abruptly and the chromaticity difference Δx assumed a maximum both at an irradiation intensity of 475 $mJ/cm^2$. Consequently, the local microcrystallization intensity in the judgment regions 23a to 23c was determined to be 470 $mJ/cm^2$, whereas the local microcrystallization intensity in the judgment regions 23d and 23e was determined to be 475 $mJ/cm^2$.

In the present embodiment, the local microcrystallization intensities obtained in the groups of judgment regions 23a to 23e were averaged, and the microcrystallization intensity was determined to be 472 $mJ/cm^2$. The average was derived from the calculation: 470×(3/5)+475×(2/5)=472. In this case, the range of in-plane variation in the irradiation intensity was evaluated to be around 1.1% based on the, calculation (475−470)/472. It is to be noted that it is also possible to select, for example, the lowest one of the above local microcrystallization intensities in determination of the microcrystallization intensity.

In the above example, the microcrystallization intensity was determined by averaging the local microcrystallization intensities measured for the plurality of groups of judgment regions 23a to 23e provided in the preliminary irradiation areas 21. Consequently, possible errors due to the range of in-plane variation in tie irradiation intensity can be reduced in the determination of microcrystallization intensity. It is preferable for the area of each judgment region 23 to occupy 1% or more of the area of the corresponding preliminary irradiation area 21 in order to determine the accurate microcrystallization intensity. Finder, in the above embodiment, five judgment regions 23 were provided, whereas, if there are more judgment regions provided, the microcrystallization intensity can be more accurately determined.

It is to be noted that if a single shot of pulse laser at the irradiation intensity higher than the microcrystallization intensity is irradiated on the surface of the amorphous-Si film, the region irradiated with the pulse laser is microcrystallized. However, in the relatively narrow regions around the irradiated region of the amorphous-Si film, the temperature therein is higher than the melting temperature and lower than the temperature for the microcrystallization intensity, causing the regions to be crystallized without the microcrystallization. The same holds true for the case that the pulse laser is irradiated on the already microcrystallized regions before the irradiation, because the polycrystalline-Si film is melted and recrystallized through the irradiation of the pulse laser. Thus, if scanning irradiation is conducted at such an irradiation intensity over the microcrystallization intensity, crystallized regions having a large grain size periodically occur in the microcrystallized region.

Thus, a larger scanning pitch will provide a larger ratio of the area of the microcrystallized region relative to the area of the crystallized region, thereby allowing the change in the chromaticity at the microcrystallization intensity to be significant. In particular, a scanning pitch of 0.01 mm or more will provide a significant change in the chromaticity at the microcrystallization intensity, thereby facilitating the determination of the microcrystallization intensity.

A second example based on the method of judging the grain size uniformity in the second embodiment will now be described. An irradiation intensity of 450 m/cm$^2$, which is lower than the microcrystallization intensity, was adopted for the actual irradiation in the second example, based on the microcrystallization intensity of 472 mJ/cm$^2$ and the range of in-plane variation of 1.1% in the irradiation intensity, which were obtained in the first example. At this irradiation intensity, the actual irradiation was performed on the substrate for a product to melt and recrystallize an amorphous-Si film, whereby a polycrystalline-Si film was formed. As in the case of the preliminary irradiation, the lasing frequency of the pulse laser was set to 300 Hz, and the dimensions of the irradiated laser beam were 350 mm (in y-direction)×0.4 mm (in x-direction). The scanning pitch was set at 0.04 mm.

While the surface-light source unit 14 irradiated the target irradiation area, the charge coupled device 17 picked-up the image of the target irradiation area in block. The chromaticity of the target irradiation area was measured according to the thus picked-up image data. It was confirmed from the obtained chromaticity that the microcrystallization has not yet been caused and the grain size was relatively large. Further, a plurality of judgment regions were set in the target irradiation area, and the range of chromaticity variation of the judgment region was calculated resulting in that there was a small range of variation. Thus, it was confirmed that the size of the crystal grin was uniform in the in-plane direction of the film because of a smaller range of in-plane variation in the irradiation intensity of the pulse laser and the process conditions for forming the film.

Subsequently, TFT devices were fabricated. The average carrier mobility was 260 cm$^2$/Vs, and the range of variation in the threshold of the TFT devices was within 5%. Thus, it can be estimated that TFT devices having a higher performance and a smaller range of characteristic variation were achieved by the laser irradiation process of the first embodiment described above.

In the above-described examples, although the irradiation intensity in the actual irradiation was lower than the microcrystallization intensity, the present invention is not limited to use of an irradiation intensity lower than the microcrystallization intensity. For instance, Patent Publication JP-2003-332346A describes a method of controlling the locations for forming crystal grains by irradiation of laser at an irradiation intensity above the microcrystallization intensity at a predetermined interval prior to formation of a polycrystalline-Si film. Although this process is different from a typical process for forming the polycrystalline-Si film, an accurate microcrystallization intensity should be determined also in this technique, in order to form more reliable crystal grains. In this technique, the laser irradiation process described in the first embodiment and first example of the present invention may be preferably used.

In accordance with the first exemplary embodiment of the present invention, the illumination of the irradiation areas in block as well as the receipt of the reflected light from the irradiation are in block does not require moving device for moving the stage mounting thereon the substrate, light source for illumination and charge coupled device for receiving the reflected light, to simplify the structure of the laser irradiating apparatus, and also improves the through during the judgment of the microcrystallization intensity.

The present invention has been described based on its preferred embodiments as described above. The laser irradiation process and laser irradiation apparatus of the present invention are by no means restricted to the configurations of the above embodiments, and a laser irradiation process and laser irradiation apparatus which are modified or altered in varies different ways from the above embodiments will fall within the scope of the present invention.

What is claimed is:

1. A method comprising:
    scanning a semiconductor film on a substrate with laser having a specific lasing frequency at a plurality of irradiation intensities to form a plurality of irradiation areas on the semiconductor film each corresponding to one of said irradiation intensities;
    illuminating said plurality of irradiation areas in block to receive light reflected from said irradiation areas in block;
    judging a microcrystallization intensity based on said received reflected light;
    determining an irradiation intensity based on said microcrystallization intensity;
    scanning another semiconductor film with laser having said lasing frequency at said determined irradiation intensity to form a crystallized film; and
    forming a semiconductor device on said crystallized film, wherein said judging includes:
    comparing chromaticities of said received reflected light measured for said irradiation areas, against one another;
    detecting a maximum change in the chromaticity per unit change of said irradiation intensity; and
    determining said microcrystallization intensity based on said maximum change.

2. The method according to claim 1, wherein said judging further includes:
    determining a plurality of judgment areas in each of said irradiation areas, each of said judgment areas in each of said irradiation areas corresponding to one of said judgment areas of the others of said irradiation areas to form a group of said judgment areas;
    comparing image data of corresponding said judgment areas in each group against one another to detect the maximum change in the chromaticity per unit change of said irradiation intensity in the each group;
    selecting one of said maximum changes per unit change of said irradiation intensity obtained in a plurality of said group; and
    determining said microcrystallization intensity based on said selected maximum change.

3. The method according to claim 2, further comprising judging a range of variation in an irradiation intensity of said laser based on a range of variation detected in said maximum changes per unit change of said irradiation intensity.

4. The method according to claim 2, wherein said judgment areas each have an area equal to or above 1% of an area of said each of said irradiation area.

5. The method according to claim 1, wherein said illuminating uses a surface light source.

6. The method according to claim 1, wherein said another semiconductor film is formed on said substrate.

7. The method according to claim 1, wherein said another semiconductor film is formed on another substrate.

8. The method according to claim 1, wherein said semiconductor film is an amorphous silicon film, and said crystallized film includes polycrystalline silicon.

9. The method according to claim 1, wherein said plurality of irradiation intensities have a stepwise difference therebetween.

10. A laser irradiation apparatus using the method according to claim 1, comprising a laser source unit for emitting said laser, an optical system for shaping said laser into a specified shape having specified dimensions, a surface light source for emitting light for said illuminating, and a charge coupled device for receiving said reflected light.

11. The laser irradiation apparatus according to claim 10, wherein said surface light source emits surface light having a range of variation equal to or below 5% in an in-plane luminance.

12. A method comprising:
scanning a semiconductor film on a substrate with laser having a specific lasing frequency at a plurality of irradiation intensities to form a plurality of irradiation areas on the semiconductor film each corresponding to one of said irradiation intensities;
illuminating said plurality of irradiation areas in block to receive light reflected from said irradiation areas in block;
measuring chromaticity of said received reflected light for each of said irradiation areas to detect a microcrystallization intensity based on said measured chromaticity;
scanning another semiconductor film with laser having said lasing frequency at said determined irradiation intensity to form a crystallized film; and
forming a semiconductor device on said crystallized film, wherein said judging includes:
comparing chromaticities of said received reflected light measured for said irradiation areas, against one another;
detecting a maximum change in the chromaticity per unit change of said irradiation intensity; and
determining said microcrystallization intensity based on said maximum change.

13. A laser irradiation apparatus using the method according to claim 12, comprising a laser source unit for emitting said laser, an optical system for shaping said laser into a specified shape having specified dimensions, a surface light source for emitting light for said illuminating, and a charge coupled device for receiving said reflected light.

14. The laser irradiation apparatus according to claim 13, wherein said surface light source emits surface light having a range of variation equal to or below 5% in an in-plane luminance.

* * * * *